United States Patent [19]
Viskup

[11] Patent Number: 5,443,386
[45] Date of Patent: Aug. 22, 1995

[54] TOOTHBRUSH AND METHOD FOR TREATMENT OF PERIODONTAL DISEASE

[76] Inventor: John H. Viskup, 106 Main St., Vergennes, Vt. 05461

[21] Appl. No.: 116,696

[22] Filed: Sep. 7, 1993

[51] Int. Cl.⁶ .............................................. A61C 15/00
[52] U.S. Cl. ................................ 433/216; 601/164; 601/165
[58] Field of Search ................... 433/80, 81, 216, 224; 128/62 A, 66

[56] References Cited

U.S. PATENT DOCUMENTS

| | | | |
|---|---|---|---|
| 1,586,262 | 5/1926 | Noble | 128/62 A |
| 3,874,084 | 4/1975 | Cole | 128/62 A |
| 4,560,351 | 12/1985 | Osborne | 433/80 |
| 4,724,570 | 2/1988 | Hitzman | |
| 4,776,054 | 10/1988 | Rauch | |
| 4,903,688 | 2/1990 | Bibby et al. | 433/216 |
| 5,175,901 | 1/1993 | Rabinowitz | 128/62 A |

*Primary Examiner*—Nicholas D. Lucchesi
*Attorney, Agent, or Firm*—Dickinson, Wright, Moon, Van Dusen & Freeman

[57] ABSTRACT

A customized tooth cleansing device equipped with bristles whose orientation, length, and flexibility is customized to the dental characteristics of the user so as to provide proper penetration of the periodontal pockets. The device is equipped with a conduit for irrigating the mouth of the user with a cleansing, medicinal, or antibiotic solution. The device is molded to accommodate the particular dental characteristics of the user, and is equipped with a seal to prevent escape of the irrigating solution.

21 Claims, 1 Drawing Sheet

TOOTHBRUSH AND METHOD FOR TREATMENT OF PERIODONTAL DISEASE

FIELD OF THE INVENTION

This invention relates to a toothbrush for prescription by a dentist for cleaning teeth and gingival crevices and massaging the free marginal gingiva, and to a method for making such a toothbrush.

BACKGROUND OF THE INVENTION

Numerous toothbrushes and tooth cleansing devices have been proposed in the prior art. These toothbrushes do not adequately clean all of the surfaces and fissures of the teeth, and in particular, fail to penetrate and clean the periodontal area. Furthermore, most conventional toothbrushes do not adequately massage the gingival tissues. As a result, these devices provide inadequate dental hygiene.

A number of prior art devices have sought to improve upon the conventional toothbrush. U.S. Pat. No. 4,724,570 (Hitzman) discloses a toothbrush with multi-tufted bristles designed to clean exposed areas of the user's teeth as well as areas below the gum line. U.S. Pat. No. 4,776,054 (Rauch) discloses a toothbrush having bristles that are oriented in various directions to provide increased cleaning of interdental areas and improved gum massage.

While these hand-held toothbrushes represent improvements over prior toothbrushes, their effectiveness depends to a great degree on effective manipulation by the user. Hence, many of the possible benefits of these toothbrushes are not realized by users with poor brushing styles.

Other tooth-cleaning devices have been developed to reduce the dependency on the brushing style of the user. For example, U.S. Pat. No. 5,175,901 (Rabinowitz) discloses a U-shaped device which fits over an entire arch of teeth for cleaning all of the teeth simultaneously. U.S. Pat. No. 3,874,084 (Cole) discloses a device with arcuate lower and upper channels which fit over the lower and upper arches of teeth of the user. The channels are individually molded to fit the curvature of the user's jaws and are custom fitted with bristles in an orientation to cleanse the teeth and provide for penetration and cleansing of the gingival crevice. However, this device, which relies on the chewing motion of the user's jaws to manipulate the bristles, provides ineffective cleansing action. Furthermore, the design of this device causes the hardened housing of the device to come into contact with the free marginal gingiva, a result particularly undesirable in the case of users with sore or inflamed gingival tissues. Finally, the contact between the housing and the free marginal gingiva prevents the bristles from adequately penetrating and cleansing the gingival crevice.

SUMMARY OF THE INVENTION

The present invention is a highly effective tooth cleansing device that is particularly designed to be customized so that the bristles penetrate the periodontal pockets to the proper depth to ensure proper cleansing. The specifications for the toothbrush are prescribed by a dentist after he has completed a thorough periodontal examination. Furthermore, the toothbrush of the present invention allows the bristles to be replaced or interchanged with other bristles of different size, stiffness and flexibility, whereby the dentist may alter the dental care as the patient's oral health dictates.

The toothbrush of the present invention is also capable of use in combination with hygienic and therapeutic irrigation appliances to effectively deliver various oral rinses, bactericidal agents or antibiotic agents to the proper areas of the user's dentition and periodontium and for the proper length of time.

A chief advantage of the present invention is that it provides a toothbrush which allows the user to correctly clean and maintain the health of his dentition and periodontium with greater ease and effectiveness and in less time than with a conventional toothbrush, without using any special techniques. This feature is particularly useful for patients with physical or mental handicaps that might otherwise interfere with their brushing technique.

PREFERRED EMBODIMENTS OF THE INVENTION

Figure 1:
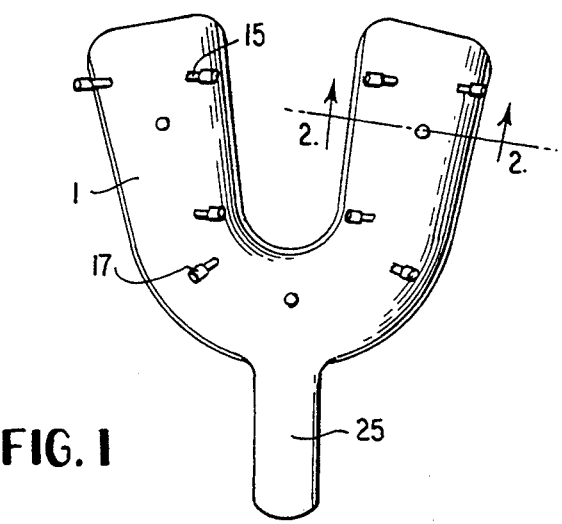
FIG. 1 is a top plan view of a preferred embodiment of the invention.
Figure 2:
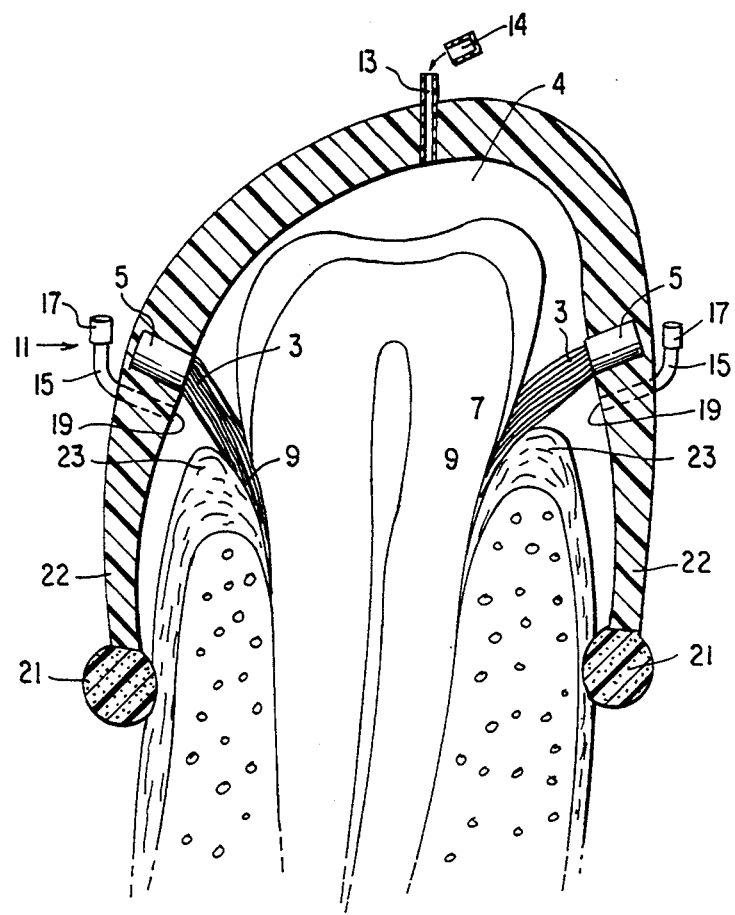
FIG. 2 is a bottom plan view of the embodiment of FIG. 1 without bristles.

As illustrated in FIGS. 1 and 2, a toothbrush in accordance with the present invention includes a customized U-shaped tray 1 for being fitted over an entire arch of teeth. The tray is made of a physiologically suitable material, preferably a chemically or light cured acrylic resin. The tray is made from a model formed by pouring standard alginate impressions of the patient's maxillary and mandibular arches with dental stone.

Figure 3:
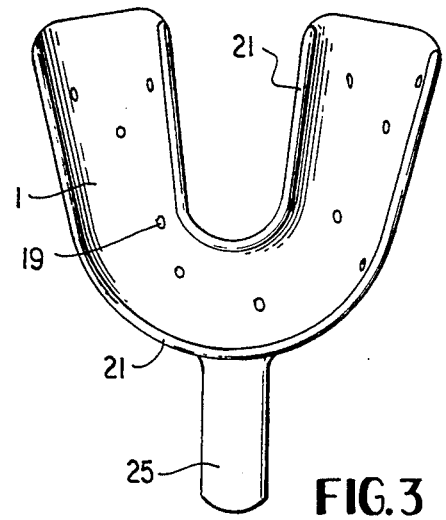
FIG. 3 is an enlarged cross section taken along line 2—2 of FIG. 1.

As illustrated in FIG. 3, the tray is fitted with individual brushes 3 which preferably extend inwardly from the tray at a distance of 2-3 mm before contacting the teeth or penetrating the gingival sulcas. The channel 4 of the tray is wide enough to allow sufficient movement of the tray with respect to the teeth for the bristles to provide proper cleansing action. Although FIG. 2 shows the tray fitted with only two individual brushes, the channel 4 of the tray may be equipped throughout with any suitable number of brushes.

The method by which the toothbrush of the present invention is constructed is as follows. The dentist makes alginate impressions of the patient's maxillary and mandibular arches. These impressions are poured with dental stone and hardened to form models of the patient's arches. A technician then uses a #4 burr to drill into the sulcus of the models at the depth and orientation prescribed by the dentist. After all the sulcular areas have been drilled to the proper depths, the lab technician inserts the tooth brush bristles into these sulcular areas and attaches their female receptacles 5. Wax or another suitable material may be used to secure the bristles and their female receptacles in place. When all of the bristles are positioned and are held in place and protected by wax, the tray material is cast over the model. This material is then cured. When the tray has hardened, the bristles will be fixed in the prescribed orientation.

The bristles are prescribed by the dentist to be of a length that will provide optimum cleaning and are set at an appropriate angle 7 with respect to the side of the channel to promote maximum cleansing of each tooth and to allow proper penetration of the gingival crevice 9. Angle 7 is preferably about 45°.

When prescribing the device of the invention for a patient with advanced periodontal disease, for example, the dentist would measure the depth of the patient's periodontal pockets. The length and orientation of the bristles would then be determined in accordance with these measurements so that they would penetrate the periodontal pockets to the depth that would provide the proper physiological effect.

The tray may further be fitted with means for interfacing the device with hygienic and therapeutic irrigation appliances (such as that sold under the trademark "Water Pik") to provide a means for irrigating the teeth with cleansing, medicinal, or antibiotic solutions. In the preferred embodiment, for example, the tray is equipped with a series of inlets 11 and outlets 13 which are capable of introducing and draining a fluid, respectively. The outlets may be fitted with caps 14 when not in use. Each inlet comprises a conduit 15 which terminates on the outer surface of the tray in an interface 17 which allows the device to be attached to hygienic and therapeutic irrigation appliances. The conduit terminates on the interior of the tray in a nozzle 19 capable of directing an irrigating fluid toward a target location. The placement of the nozzles may be customized to account for the particular dental features of the user.

The lower edges of the tray terminate in a seal 21 that prevents escape of the oral rinse material or dentifrice. The seal is preferably made of a soft flexible material to provide a cushion between the channel and the delicate tissues of the mouth. Since the sides 22 of the tray extend over the free marginal gingiva 23, they do not interfere with the ability of the bristles to penetrate the gingival crevice. Furthermore, since the seal comes into contact with the gums below the free marginal gingiva, the device of the present invention avoids irritation of these tissues.

The tray is equipped with a handle 25 which allows the user to manipulate the device manually. Alternately, the device may be equipped with motorized means of moving or vibrating the tray.

Modifications within the scope of the appended claims will be apparent to those of skill in the art.

What is claimed is:

1. A customized tooth cleansing device comprising:
   a U-shaped tray customized to the user's maxillary or mandibular arch for fitting over the maxillary or mandibular arch of the user; and
   at least one receptacle means embedded in said tray, said at least one receptacle means removably holding at least one cleaning bristle at a predetermined orientation and depth such that said at least one cleaning bristle in each receptacle is oriented toward a specific periodontal pocket of the user.

2. The device of claim 1, wherein said U-shaped tray is formed from an acrylic resin.

3. The device of claim 1, wherein the orientation and of said at least one bristle is set in accordance with measurements made on the depth of a periodontal pocket in the user's mouth.

4. The device of claim 1, wherein said U-shaped tray is further equipped with means for irrigating the mouth of the user with a cleansing, medicinal, or antibiotic solution.

5. The device of claim 4, wherein the edges of the U-shaped tray terminate in a seal capable of preventing the escape of oral rinse material.

6. The device of claim 4, wherein the means for irrigating the mouth of the user with a cleansing, medicinal, or antibiotic solution comprises a series of inlets capable of interfacing with a hygienic and therapeutic irrigation appliance.

7. The device of claim 6, wherein the U-shaped tray is further equipped with means for draining fluids from the mouth of the user.

8. A method of making a toothbrush or a part thereof, comprising the steps of:
   providing a model of at least a portion of a patient's maxillary or mandibular arch;
   measuring the depth and orientation of at least one periodontal pocket in the portion of the patient's mouth corresponding to the model;
   providing at least one hole in the model at a point corresponding to said at least one periodontal pocket, and at the same depth and orientation as said at least one periodontal pocket;
   inserting into said hole cleansing means for cleansing teeth; and
   providing said at least one hole and said cleansing means with holding means for holding said cleansing means in the orientation of said hole, wherein said holding means is removable from said model.

9. The method of claim 8, wherein said cleansing means comprises bristles.

10. The method of claim 9, wherein a portion of said bristles extending from said at least one hole is capped with a female receptacle.

11. The method of claim 8, wherein said cleansing means is further capable of penetrating the periodontal pockets of a patient.

12. The method of claim 8, wherein the impression of the patient's maxillary or mandibular arch is an alginate impression.

13. The method of claim 8, wherein said step of providing a model further comprises the steps of:
   (a) making an impression of at least a portion of a patient's maxillary or mandibular arch; and
   (b) creating said model by pouring dental stone into the impression and allowing it to harden.

14. The method of claim 8, further comprising the further step of removing said holding means from said model and equipping said holding means with a handle.

15. The method of claim 8, wherein said holding means is a resin capable of hardening sufficiently to be removed from the model and being incorporated into a toothbrush.

16. The method of claim 15, wherein said resin is an acrylic resin.

17. A method of making a toothbrush or a part thereof, comprising the steps of:
   (a) providing a model of at least a portion of a patient's maxillary or mandibular arch;
   (b) creating at least one hole in the model;
   (c) inserting into the at least one hole cleansing means for cleansing teeth;
   (d) covering at least a portion of the model containing the hole with a material which hardens over time into a physiologically acceptable mass;
   (e) removing the hardened, physiologically acceptable mass from the model; and
   (f) incorporating the physiologically acceptable mass into a device for cleaning teeth.

18. The method of claim 17, further comprising the steps of:

determining the optimal orientation and depth at which the cleansing means should penetrate the gingival sulcas at a given point on the patient's maxillary or mandibular arch; and creating the at least one hole at the same orientation and depth at the corresponding point on the model.

19. The method of claim 17, wherein the physiologically acceptable mass becomes sufficiently hard over time to permanently hold the cleansing means in the orientation of the at least one hole.

20. A tooth cleansing device made according to the method of claim 17.

21. A tooth cleansing device made according to the method of claim 18.

* * * * *